(12) United States Patent
Jones

(10) Patent No.: US 9,833,645 B2
(45) Date of Patent: Dec. 5, 2017

(54) PERSONAL AIR FILTER

(71) Applicant: Faith K. Jones, Arlington, VA (US)

(72) Inventor: Faith K. Jones, Arlington, VA (US)

( * ) Notice: Subject to any disclaimer, the term of this patent is extended or adjusted under 35 U.S.C. 154(b) by 268 days.

(21) Appl. No.: 14/398,618

(22) PCT Filed: May 24, 2013

(86) PCT No.: PCT/US2013/042573
§ 371 (c)(1),
(2) Date: Nov. 3, 2014

(87) PCT Pub. No.: WO2013/181080
PCT Pub. Date: Dec. 5, 2013

(65) Prior Publication Data
US 2015/0174435 A1    Jun. 25, 2015

Related U.S. Application Data

(60) Provisional application No. 61/652,162, filed on May 26, 2012.

(51) Int. Cl.
| | |
|---|---|
| *A62B 7/10* | (2006.01) |
| *A62B 23/02* | (2006.01) |
| *A62B 18/08* | (2006.01) |
| *A62B 18/00* | (2006.01) |
| *A62B 9/00* | (2006.01) |
| *A62B 9/06* | (2006.01) |
| *A62B 18/02* | (2006.01) |

(Continued)

(52) U.S. Cl.
CPC ......... *A62B 18/084* (2013.01); *A61M 16/107* (2014.02); *A62B 7/10* (2013.01); *A62B 9/006* (2013.01); *A62B 9/06* (2013.01); *A62B 18/003* (2013.01); *A62B 18/02* (2013.01); *A62B 18/088* (2013.01); *A62B 18/10* (2013.01); *A62B 23/025* (2013.01); *A62B 23/06* (2013.01); *A61M 16/0683* (2013.01); *A61M 16/208* (2013.01)

(58) Field of Classification Search
CPC ....... A62B 18/084; A62B 18/02; A62B 18/10; A62B 16/208; A62B 7/10; A62B 9/06; A62B 19/00; A62B 23/025; A62B 23/02
USPC ............. 128/205.27, 206.13, 206.15, 206.17
See application file for complete search history.

(56) References Cited

U.S. PATENT DOCUMENTS 3,142,549 A * 7/1964 Klusewitz .............. A62B 23/02
128/206.17
4,915,105 A * 4/1990 Lee ........................ A62B 18/00
128/205.27
(Continued)

*Primary Examiner* — Kristen Matter

(57) ABSTRACT

A personal air filter device with an air filter assembly retained in the air filter holding member is disclosed. An ear support member is attached to the air filter holding member and can be hung over the ear of the user to support the air filter holding member. Alternatively, a clip member attached to the air filter holding member can be utilized to attach the device to the user's clothing or accessories. An air tube assembly extends from the air filter holding member to the mouthpiece for the purpose of breathing filtered air flowing through the air filter assembly. An air intake check valve situated near the end of the air tube attached to a mouthpiece retaining member and an air outflow check valve situated near the outer surface of the mouthpiece retaining member to ensure exhaled air is directed out of the device and is not reinhaled.

24 Claims, 17 Drawing Sheets

(51) Int. Cl.
  *A62B 18/10*   (2006.01)
  *A62B 23/06*   (2006.01)
  *A61M 16/10*   (2006.01)
  A61M 16/06    (2006.01)
  A61M 16/20    (2006.01)

(56) References Cited

U.S. PATENT DOCUMENTS

| | | | | |
|---|---|---|---|---|
| 4,996,983 | A * | 3/1991 | AmRhein | A62B 18/00 |
| | | | | 128/205.29 |
| 5,086,768 | A * | 2/1992 | Niemeyer | A62B 9/06 |
| | | | | 128/205.24 |
| 5,415,675 | A * | 5/1995 | Powers | A61L 9/12 |
| | | | | 261/DIG. 88 |
| 6,550,479 | B1 * | 4/2003 | Duxbury | A62B 7/10 |
| | | | | 128/205.27 |
| 6,619,288 | B2 * | 9/2003 | Demers | A61M 16/06 |
| | | | | 128/205.25 |
| 8,574,331 | B2 * | 11/2013 | Bangera | A62B 23/025 |
| | | | | 128/201.23 |
| 8,887,725 | B2 * | 11/2014 | Hernandez | A61M 16/06 |
| | | | | 128/205.25 |
| 2005/0241642 | A1 * | 11/2005 | Krzysztofik | A62B 23/02 |
| | | | | 128/206.15 |
| 2006/0193142 | A1 * | 8/2006 | Dupre | F21S 8/026 |
| | | | | 362/418 |
| 2006/0231100 | A1 * | 10/2006 | Walker | A61M 16/08 |
| | | | | 128/205.25 |
| 2007/0137650 | A1 * | 6/2007 | Chan | A62B 18/025 |
| | | | | 128/205.27 |
| 2009/0000618 | A1 * | 1/2009 | Warren | A61M 16/0666 |
| | | | | 128/202.13 |
| 2010/0108071 | A1 * | 5/2010 | Macy, Jr. | A61M 16/0666 |
| | | | | 128/206.11 |

* cited by examiner

PERSONAL AIR FILTER

CROSS REFERENCE TO RELATED APPLICATIONS

This application claims the benefit of U.S. Provisional Patent Application No. 61/652,162, filed May 25, 2012, the disclosure of which is incorporated by reference.

FIELD OF INVENTION

This invention relates generally to air filtering apparatus and, more particularly to a personal air filtering apparatus.

BACKGROUND OF THE INVENTION

According to the World Health Organization (WHO), urban outdoor air pollution is estimated to cause 1.3 million deaths worldwide per year. Those living in middle-income countries disproportionately experience this burden. The American Heart Association states that air pollutants contribute measurably and significantly to both acute and chronic cardiovascular and pulmonary disease. Air pollutants are comprised of particulate matter and other gaseous chemicals that can be harmful to a person's health when inhaled. The outdoor air pollution in many cities around the world far exceeds the WHO recommended levels for health, containing an unsafe amount of particulate matter and potentially toxic gasses because of the emissions generated by the heightened industrial activity and vehicle emissions in and around those cities.

To protect themselves from breathing these harmful pollutants, some people wear respirator type masks while outdoors. These masks can either be simple cloth scarves that are wrapped around the user's nose and mouth, or more advanced masks such as an N95 disposable particulate respirator.

Although respirator masks are in common use, they have a number of disadvantages. They are visually unsightly and feel restrictive because they tend to cover a major portion of the user's face, usually extending from the lower chin, over the mouth and nose and ending just under the user's eyes. Wearing a mask carries a stigma as other people may assume that the user is ill and attempt to avoid contact with them. Without a proper fitting, it is difficult to achieve a tight seal around the user's face with facemask respirators (and nearly impossible to achieve a proper seal if the user has facial hair, facial deformities or sensitive skin), thus allowing the user to inhale more unfiltered air and minimizing the effectiveness of the respirator. When these masks are held on by utilizing straps that wrap around the user's head, the straps tend to disturb a person's hair and also contribute to the unfavorable visual impression. For these reasons and others, many people elect not to wear a protective face mask even though, due to poor air quality, there may be a serious risk to their health from breathing the ambient air in the area where they live or work.

A number of attempts have been made to address the issues with facemask respirators described above. However, these non-mask respirators have their own drawbacks. For example, U.S. Pat. No. 4,915,105 shows a respiratory apparatus with a nostril intake manifold connected to two hoses that surround the user's head and join to one extension tube leading to a filter box attached to the user's waist. U.S. Pat. No. 6,971,386 shows a device with a mouthpiece and check valves leading to two tubes that encircle the user's head with the filter cartridge placed behind the user's head on the upper back or neck. The device balances on the user's shoulders and is held on by biting the mouthpiece. Each of the above devices wrap around the user's head and are difficult to manage and unwieldy to use in daily activities. They are also visually obtrusive and unattractive. Further, the distance of the filter from the breath intake orifice, particularly for U.S. Pat. No. 4,915,105 and similar devices, creates a greater drag on air flow increasing the effort necessary to inhale if the device is not powered.

U.S. Pat. Nos. 5,782,234; 5,771,885 and 7,025,060 show more compact respirators where the device is held in the user's mouth and gripped by his or her teeth. The filter is located directly in front of the user's mouth and employs air flow check valves. While these mouth-held respirators avoid the larger size and unwieldiness of the previously described respirators, these mouth-held respirators have other issues. As these respirators are held in solely by force of the teeth, the respirator will fall out if the user tries to speak without removing it entirely. If the respirator is used for extended periods, the user's jaw could tire from supporting the entire weight of the device. The position of the filter protruding from the user's mouth also gives these respirators a strange appearance.

Furthermore, for nostril plug type filters (see, e.g., U.S. Pat. Nos. 7,918,225 and 6,962,156), the entire filter mechanism is inserted into the user's nostrils. These are single-use devices that must be replaced after each use, and the amount of filtration material that can be used is limited to a size that fits inside a human nostril. In addition, these nostril plug type filters do not accommodate persons who prefer to breathe through their mouth, which is often necessary when engaging in strenuous exercise.

Thus, the need exists for a personal air filter designed to minimize or eliminate one or more of these problems and to provide greater comfort and ease of use to the user, thereby increasing the likelihood that a person will wear the device and realize its health benefits.

SUMMARY OF THE INVENTION

Embodiments of a personal air filter described in this application include a wearable respirator device that does not overly obscure the user's face. The personal air filter device may attach to either the user's nose or mouth depending on their breathing preference and the embodiment chosen. It may be worn a number of ways—one embodiment utilizes the user's ear as a support member by having a piece that hooks over the user's ear, similar to an earphone, to support the device. In other embodiments, the device can be attached to the user's person or clothing by means of a clip, for instance, by clipping the device to the user's headband, necklace, shirt collar hat or other accessories. It is therefore relatively quick and easy to put on or take off and is held on by a support mechanism other than the breathing orifice. The personal air filter device is preferably foldable for compact carrying and storage. The personal air filter device also preferably allows the user to easily and quickly remove and replace the air filter assembly. The filtration material utilized in the air filter assembly may be composed of a variety of filtration materials with different filtration capabilities, including the ability to filter particulates, toxic gases and bacteria and viruses. In one embodiment, the filter can be recharged and reused. The personal air filter device also preferably allows the user to replace the pieces inserted into the user's breathing orifices, for hygiene and proper fit.

Thus, several advantages of one or more aspects are that the personal air filter device allows a wider range of people with different facial types to achieve a proper air seal. Other advantages of one or more aspects is that the personal air filter device may be more visually attractive, it is supported by means other than solely the breathing orifice, it can be used multiple times, it leaves the user's face relatively uncovered and unrestricted, the user has flexibility to choose whether they wish to breathe through their nose or mouth, it does not disturb a person's hair, the filter is not located directly in front of the user's face, and the distance from the filter to the breathing orifice is still minimized, thus allowing for ease of breathing. These and other advantages of one or more aspects will become apparent from the following descriptions, taken in connection with the accompanying drawings, wherein, by way of illustration and example, embodiments of the personal air filter are disclosed.

One embodiment of the device may be a personal respiratory device comprising: an air filter assembly with filter media; an air filter holding member; an air tube coupled to the air filter holding member; a breathing orifice interface connected to the end of the air tube which is opposite the air filter holding member; at least one air intake check valve; at least one air outflow check valve; and a member that connects the personal respiratory device to a user's person or clothing; wherein said air intake check valve and said air outflow check valve are capable of insuring the breathing in of filtered air and that air expelled from the user's lungs exits the device and does not flow back into the air tube; said breathing orifice interface capable of being inserted into said user's breathing orifice for the purpose of breathing filtered air flowing through said air tube wherein such filtered air has passed through the filter media located in the air filter holding member.

Another embodiment of the personal air filter device may include an air filter cartridge assembly, an air filter holding member, an ear pad, an ear support member, a first air tube member, a second air tube member, a third air tube member, a mouthpiece retaining member, a mouthpiece, an air intake check valve, air outflow check valves, said air filter cartridge assembly having stacked components including a rigid top cover member, a particulate disk filter member, an activated carbon filter disk member, a rigid lower filter retaining member and a central retaining fastener, said stacked components held together by said central retaining fastener, said filter cartridge assembly removably retained in said air filter holding member, said ear pad attached to the wall of said air filter holding member that is meant to be in contact with the user's ear, said first air tube member fixed to said air filter holding member allowing air to flow from said air filter cartridge assembly to said first air tube member, said second air tube member rotatably attached to said first air tube member, said third air tube member slidably attached in a telescoping fashion to said second air tube member, said mouthpiece retaining member rotatably attached to said third air tube member, said mouthpiece rotatably attached to said mouthpiece retaining member, said ear support member being an inverted J shape and attached at one end to said air filter holding member, said ear support member capable of being hung over the ear of said user to support said air filter holding member, said mouthpiece capable of being inserted into said user's mouth for the purpose of breathing filtered air flowing from said air filter cartridge assembly, said air intake check valve situated in said third air tube member, said air outflow check valves situated near the outer surface of said mouthpiece retaining member, and said air intake check valve and said air outflow check valves insuring the breathing in of filtered air and the expellation of exhaled air from the device.

BRIEF DESCRIPTION OF THE DRAWINGS

The drawings constitute a part of this specification and include exemplary embodiments of the personal air filter device, which may be embodied in various forms. It is to be understood that in some instances various aspects of the device may be shown exaggerated or enlarged to facilitate an understanding of the device.

DETAILED DESCRIPTION OF THE EMBODIMENTS

Detailed descriptions of certain embodiments are provided herein. It is to be understood, however, that the present personal air filter device may be embodied in various forms. Therefore, specific details disclosed herein are not to be interpreted as limiting, but rather as a basis for the claims and as a representative basis for teaching one skilled in the art to employ the device.

Figure 1:
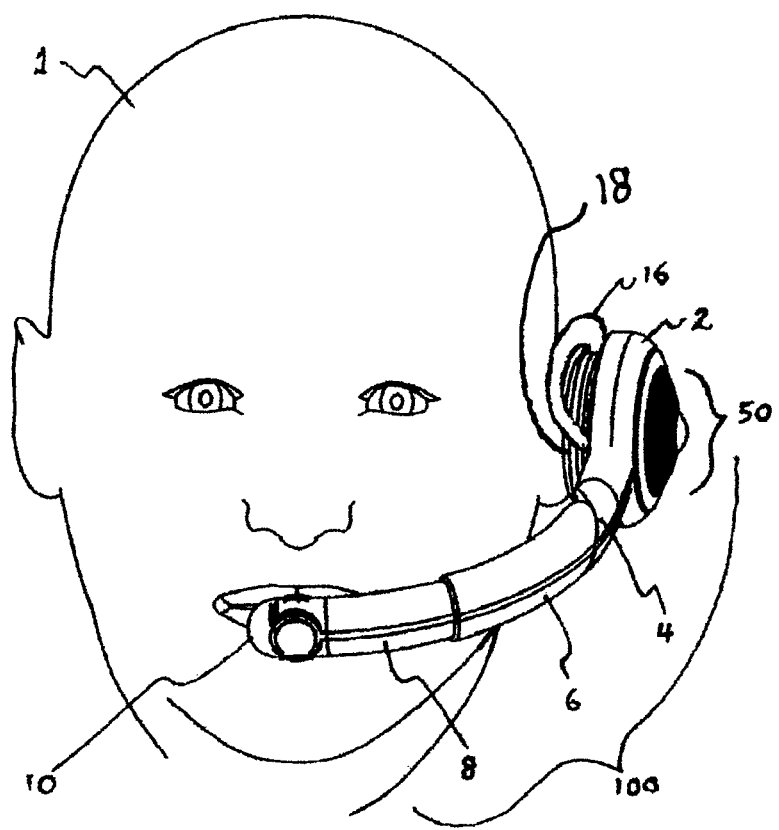
FIG. 1 is a front perspective view of a personal air filter device in accordance with various embodiments being worn by a person.
Figure 8:
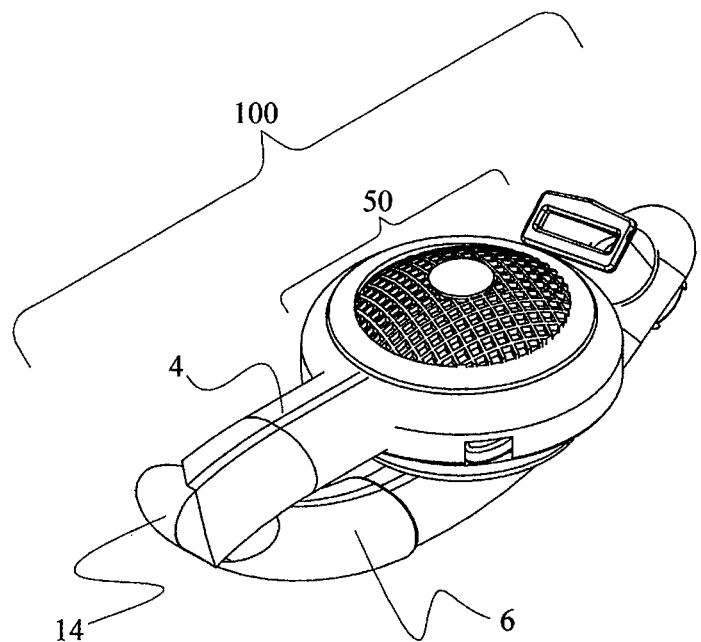
FIG. 8 is a perspective view of an embodiment of the device in the folded position.
Figure 13:
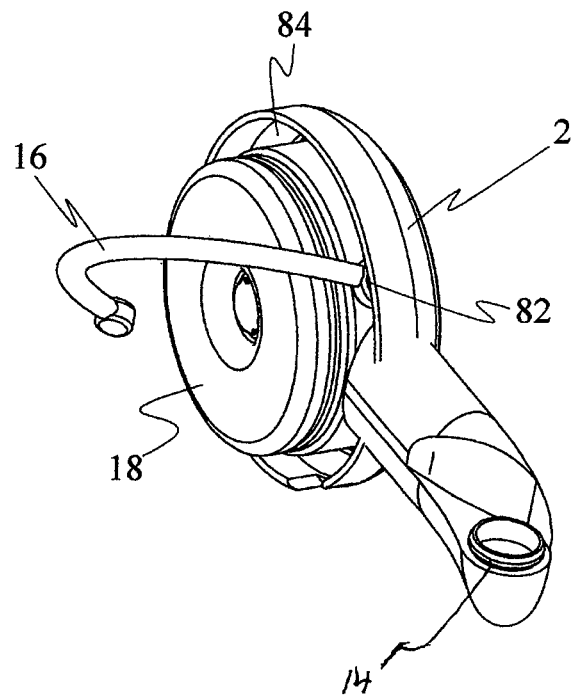
FIG. 13 is a perspective view of an ear pad and ear support member embodiment of the device.

FIG. 1 depicts a front perspective view of a person 1 wearing a personal air filter device 100 in accordance with various embodiments. An air filter holding member 2 retains an air filter cartridge assembly 50 that may be removed from the air filter holding member 2. The air filter holding member 2 includes a resilient ear pad 18 that rests against the user's ear, and the air filter holding member 2 is supported by the user's ear. FIG. 13 shows a partial perspective view of the ear pad 18 attached to the air filter holding member 2, and the ear support member 16 attached at pivot point 82. A recessed area 84 allows the inverted J shaped ear support member 16 to be stored when not in use. When in use, the ear support member 16, as shown in FIG. 13, is placed over the user's ear near where the ear meets the head. This supports the air filter holding member 2. A first air tube member 4 extends from the air filter holding member and is open on both ends, allowing air to pass from the air filter cartridge assembly 50 to the second air tube member 6 and the third air tube member 8 and finally to the mouthpiece retaining member 10 and the mouthpiece 12 (shown in FIG. 3). The joint between the first air tube member 4 and the second air tube member 6 is preferably rotatable which allows the second air tube to be folded for storage, as shown in FIG. 8. The joint between the second air tube member 6 and the third air tube member 8 is preferably a telescoping slip joint so that the user can slide the third air tube member 8 in or out depending on the size of the user's face and the distance between the user's ear and mouth. The joint between the third air tube member 8 and the mouthpiece retaining member 10 is preferably rotatable to allow the user to turn the mouthpiece retaining member 10 to the ideal angle with respect to the user's mouth. One potential effect of the personal air filter device 100 is that it does not overly detract from seeing the features of the user's face. Although the personal air filter device 100 is shown as including three air tubes, fewer tubes may be utilized in some embodiments. For example, the three air tubes 4, 6, and 8 may be consolidated into a single air tube that connects the air filter holding member 2 to the mouthpiece holding member 10. Various other configurations are also possible.

Figure 2:
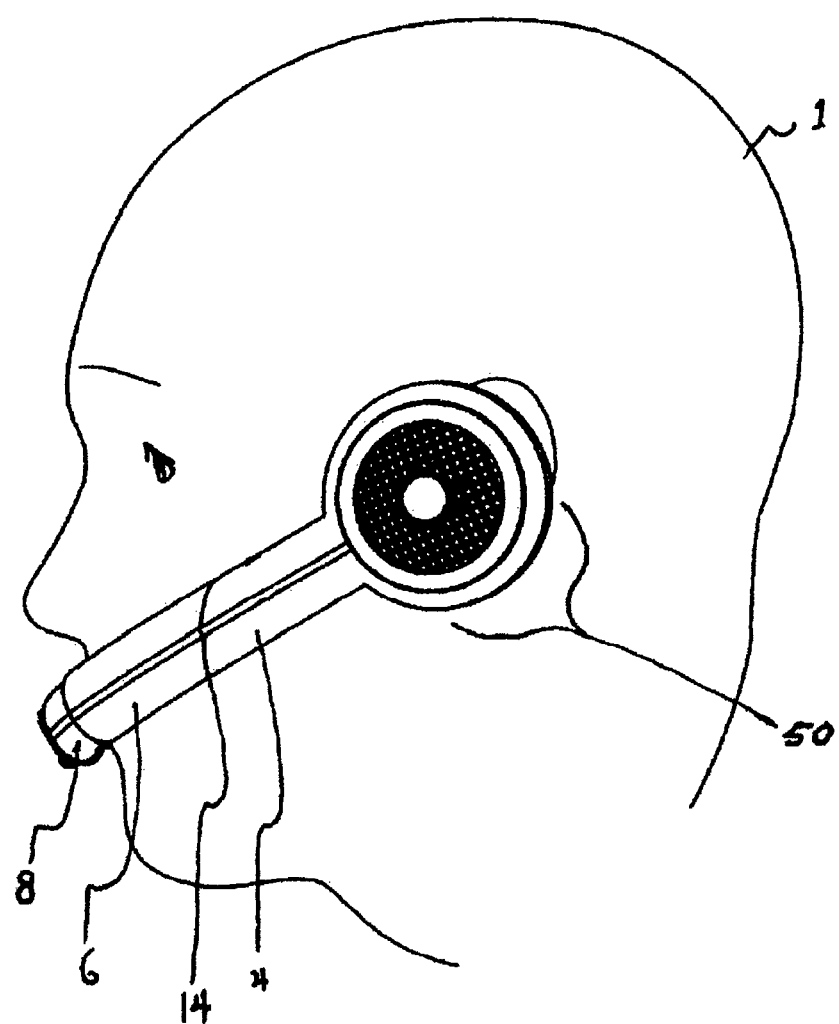
FIG. 2 is a side perspective view of an embodiment of the device being worn by a person.

FIG. 2 shows a side view of a person 1 wearing the personal air filter device 100. The entire personal air filter device 100 remains in close proximity to the user's face and provides a short air travel distance from the air filter cartridge assembly 50 and the user's mouth. This relatively short distance reduces the amount of internal drag on the air passing through the tubing 4, 6 and 8. Rotatable joint 14 can be clearly seen and is the folding point for when the personal air filter device 100 is not in use and is folded for storage.

Figure 3:
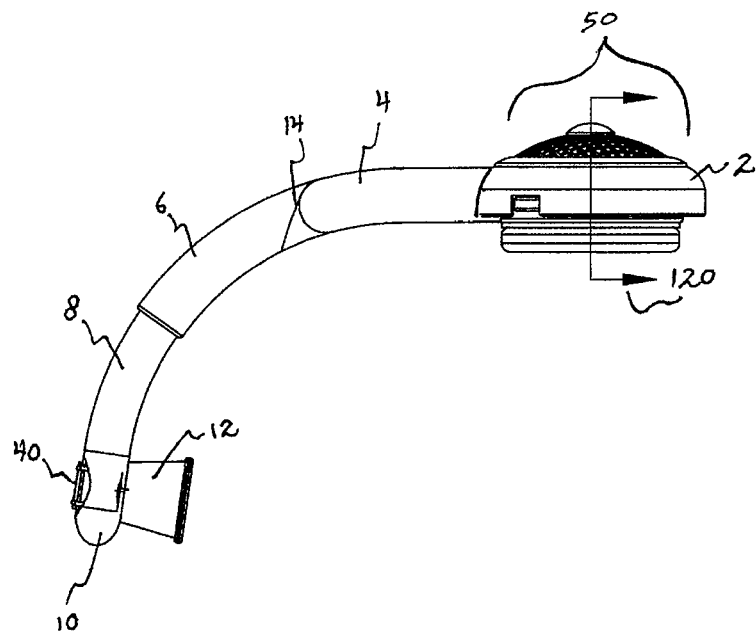
FIG. 3 is a side view of an embodiment of the device.

FIG. 3 shows a side view of the personal air filter device 100. In this view the mouthpiece 12 can be clearly seen. The mouthpiece 12 is snapped into the mouthpiece retaining member 10 and can swivel to allow the mouthpiece 12 to be at the correct orientation with respect to the user's mouth. The curved condition of the third air tube member 8 matches the curved condition of the second air tube member 6 so that it can be easily slid in or out to accommodate the specific distance between each user's ear and mouth.

Figure 4:
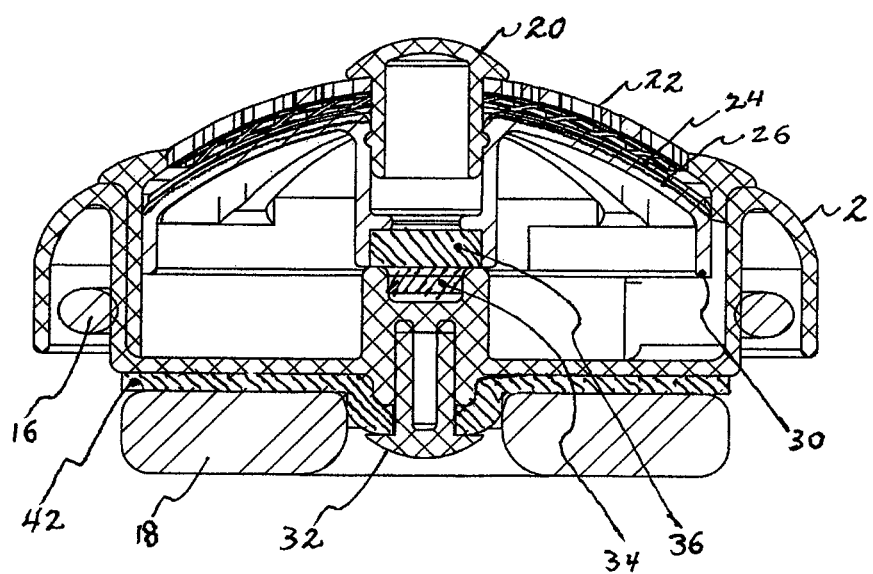
FIG. 4 is a section view of the air filter cartridge assembly and an embodiment of the air filter holding member.

FIG. 4 shows a side section view of the air filter holding member 2 and the air filter cartridge assembly 50 as defined by section line 120 shown in FIG. 3. The air filter holding member 2 includes a well that the outer walls 21 of air filter cartridge assembly 50 fits into. The air filter cartridge assembly 50 is held in place by means of a magnet 34 built into the center of the air filter holding member 2 and a ferrous metal plate 36 built into the center of the inner filter holding member 30. However, other standard means of attachment may be employed such as a snap fit, or a screw fit. A screen portion 22 protects the first filter member 24 and the second filter member 26. The filter members may be composed of a variety of filtration material. In this embodiment, the first filter member 24 is a particulate filter. The second filter member 26 is comprised of an activated carbon cloth—a material that absorbs and traps various gases, bacteria and viruses. The outside diameter of the filter pieces 24, 26 is approximately two inches in diameter, giving them enough surface area to produce effective filtering while also maintaining a sufficient airflow to permit relatively unrestricted breathing by the user. Over time, the filter members 24, 26 will become saturated and lose their effectiveness. At that time, the user can extend the life of the activated carbon cloth 26 filter by heating it at approximately 150° F. for approximately ten minutes. The particulate filter 24 can be gently washed to extend its life. Eventually, the user can replace the entire air filter cartridge assembly 50 with a new one. FIG. 4 also shows the attachment of the ear pad 18 to a rigid plate 42 which is in turn attached to the underside of the air filter holding member 2 by screw 32.

Figure 9:
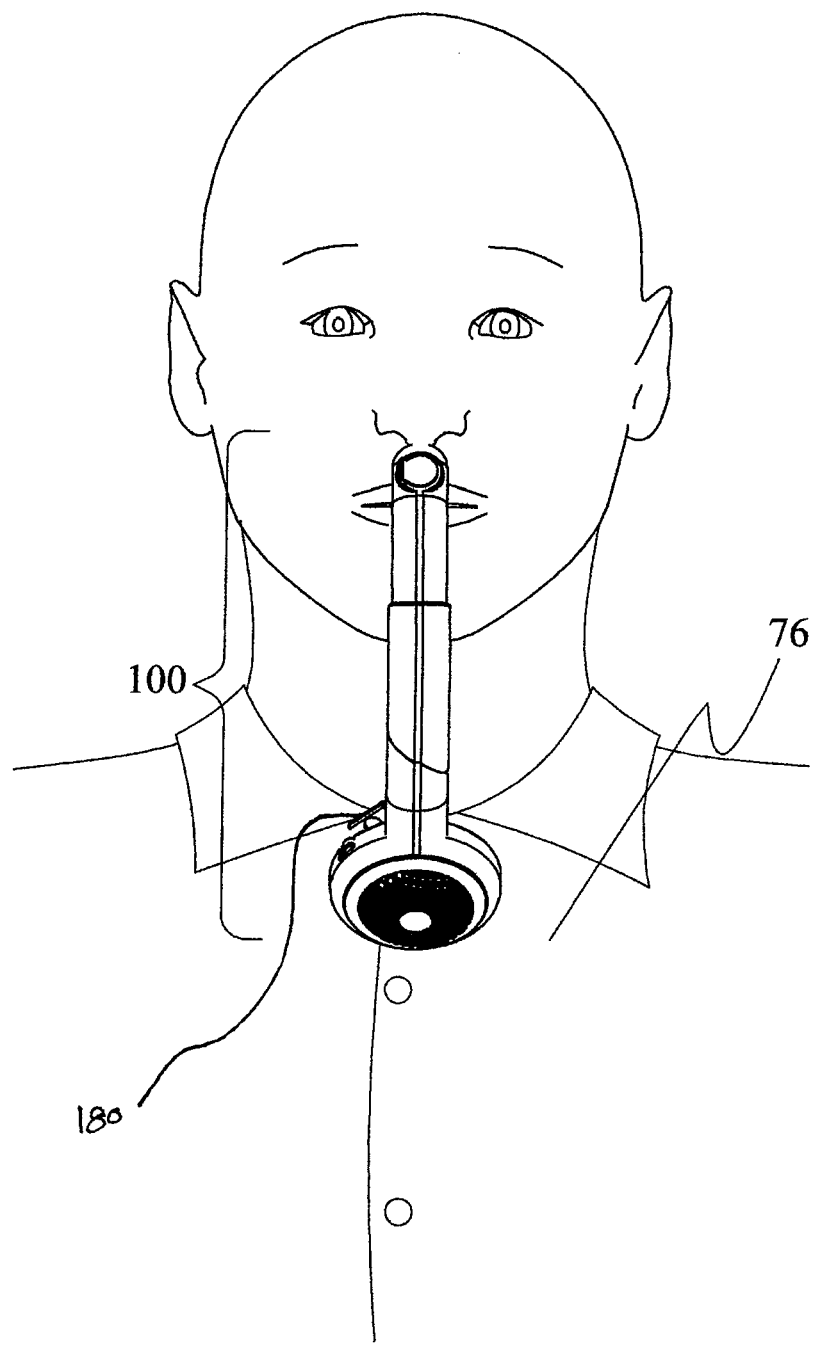
FIG. 9 is a front view of a person wearing a clip-on embodiment of the device.
Figure 10:
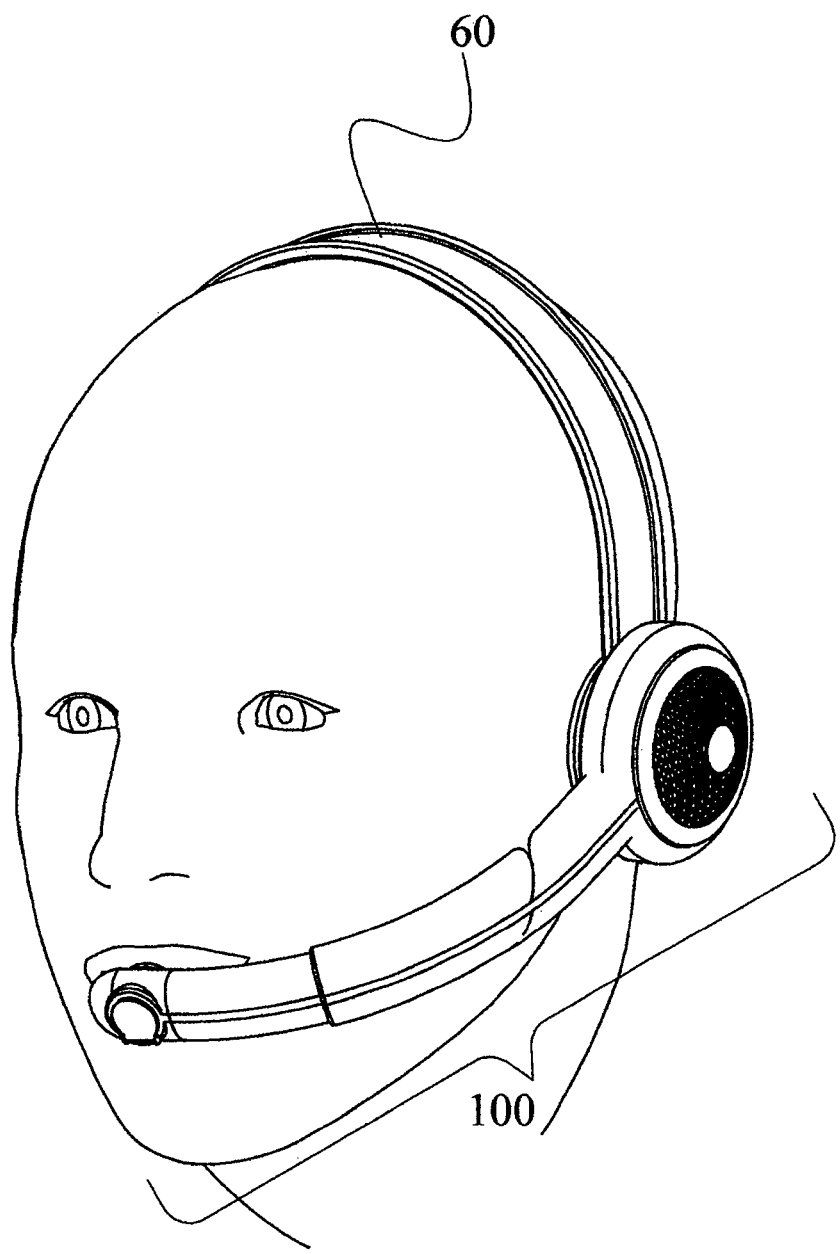
FIG. 10 is a perspective view of a person wearing an embodiment of the device utilizing a headband.
Figure 14:
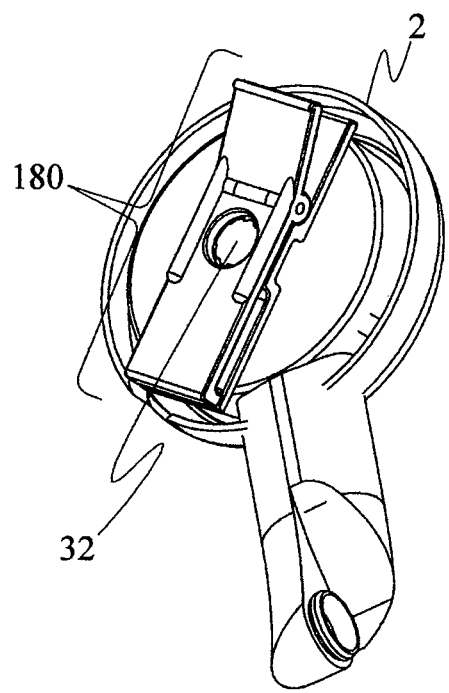
FIG. 14 is a perspective view of a clip mount version of the device in accordance with various embodiments.
Figure 15:
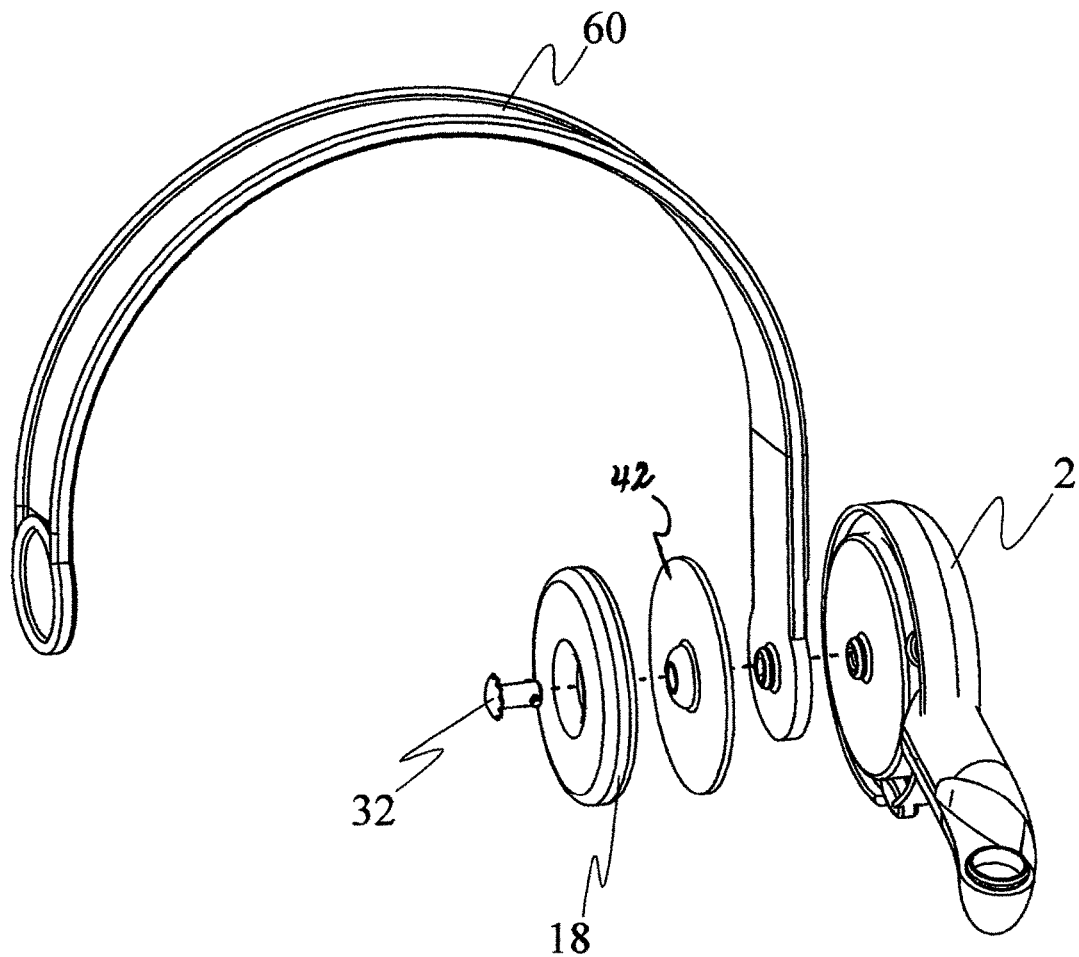
FIG. 15 is an exploded view of a headband version of the device in accordance with various embodiments.

Screw 32 can be removed by the user and at least two alternate options can be employed for wearing the personal air filter device. The first is to remove the ear pad and replace it with a clip 180, as shown in FIG. 14 so that the personal air filter device 100 can be clipped onto an item of the user's clothing such as the user's hat or shirt 76 as shown in FIG. 9. As mentioned previously, the mouthpiece 12 is capable of rotating so that it can be turned ninety degrees for use in the clip mode. The second option is to insert a headband member 60 between the back of the air filter holding member 2 and the ear pad 18 as shown in FIG. 15. This allows for a more secure fit to the user's head if so desired as shown in FIG. 10.

Figure 5:
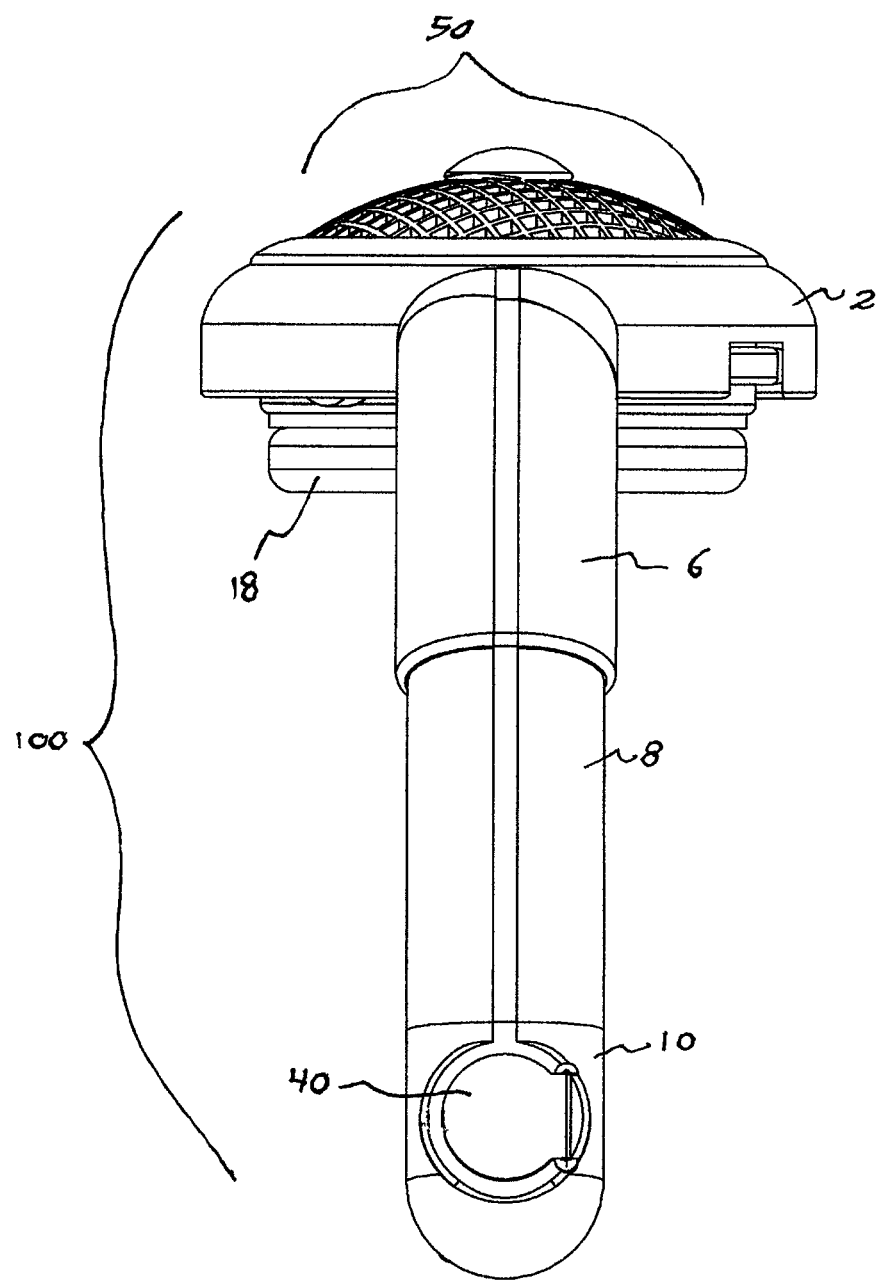
FIG. 5 is an end view of an embodiment of the device.

FIG. 5 shows an end view of the personal air filter device 100. This view shows a clear view of air outflow check valve 40. This valve opens when the user is expelling air from his or her lungs. An air intake check valve 41 is located between the mouthpiece retaining member 10 and the mouthpiece 12 as shown in the exploded view in FIG. 6.

Figure 6:
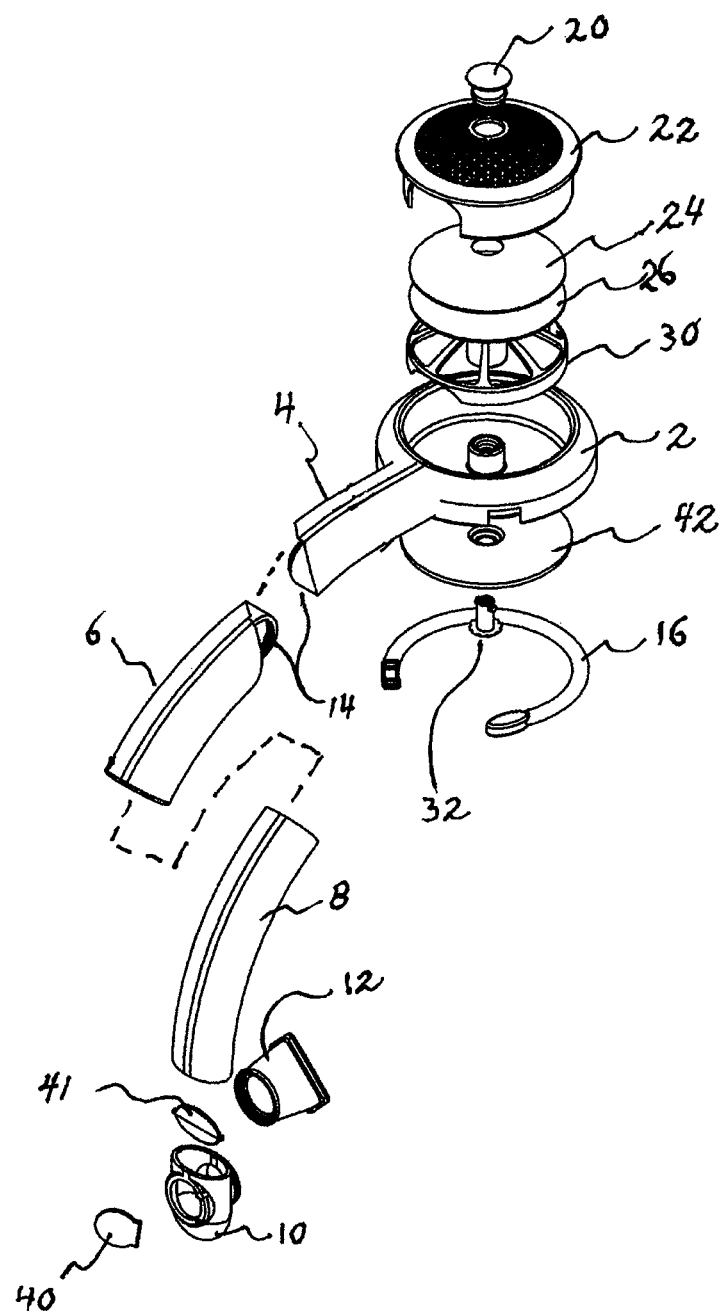
FIG. 6 is an exploded view of an embodiment of the device.

FIG. 6 shows an exploded view of the personal air filter device 100. All components of the air filter cartridge assembly, as described previously, are stacked in order. The filter discs 24, 26 are trapped in place by the upper cartridge housing 21 and the lower cartridge housing 30. The cutout 23 in the side wall of the upper cartridge housing 21 allows air to pass from the air filter cartridge assembly 50 to the first air tube member 4. The rotating joint 14 is clearly shown to be hollow to allow air to pass through it when in the use position. The upper surface of the upper cartridge housing 21 is molded in a screen pattern 22 to allow free flow of air into the air filter cartridge assembly 50 while protecting the filter material 24, 26 below it.

Figure 7:
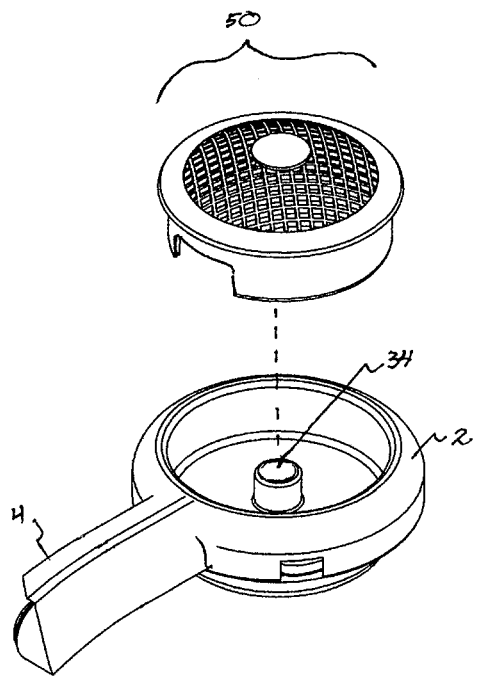
FIG. 7 is a perspective view of an embodiment of the device showing the air filter cartridge assembly removed.

FIG. 7 shows clearly the ability for the air filter cartridge assembly 50 to slide into the air filter holding member 2.

FIG. 8 shows the personal air filter device embodiment 100 in its folded form, ready for storage.

Figure 11:
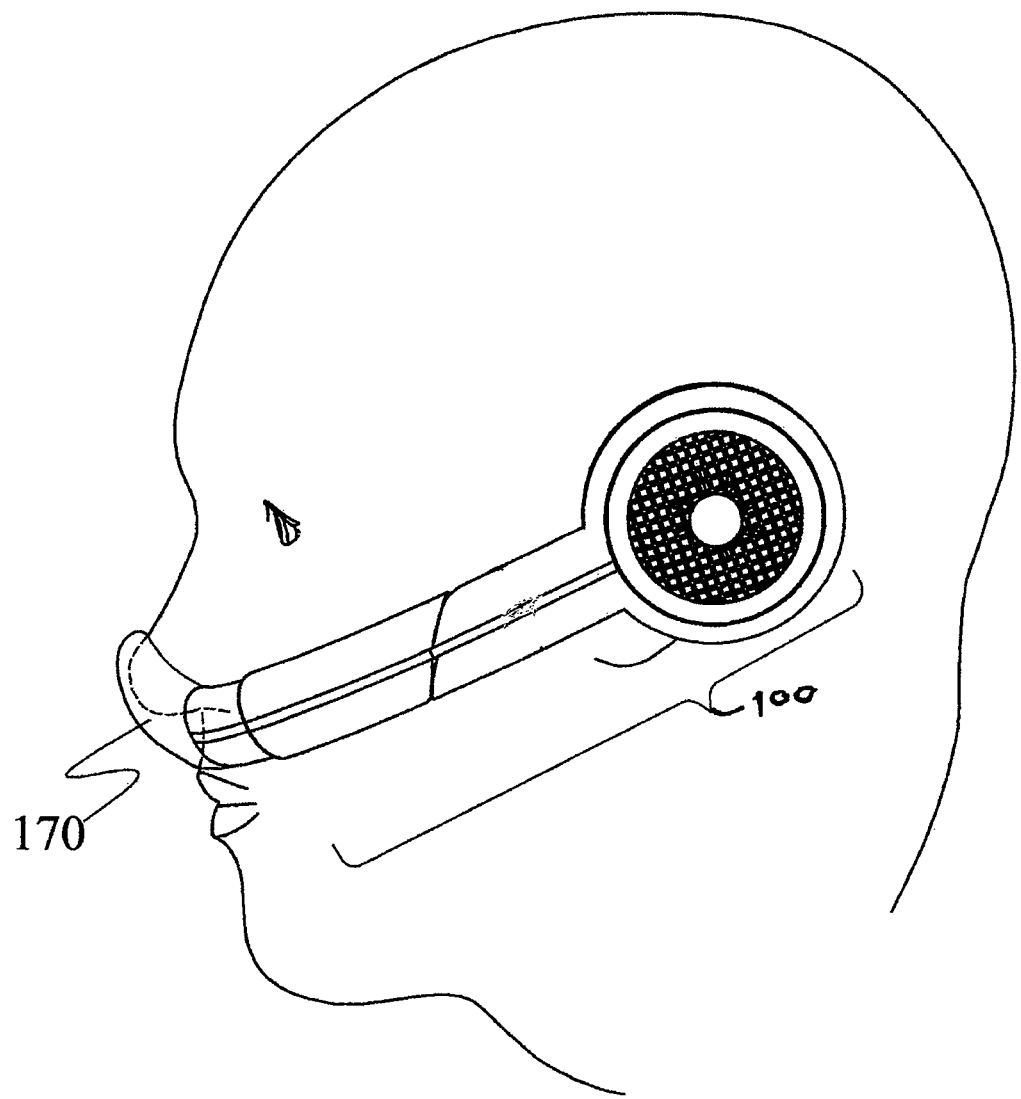
FIG. 11 is a side view of a person wearing a nose breathing version of the device in accordance with various embodiments.
Figure 12:
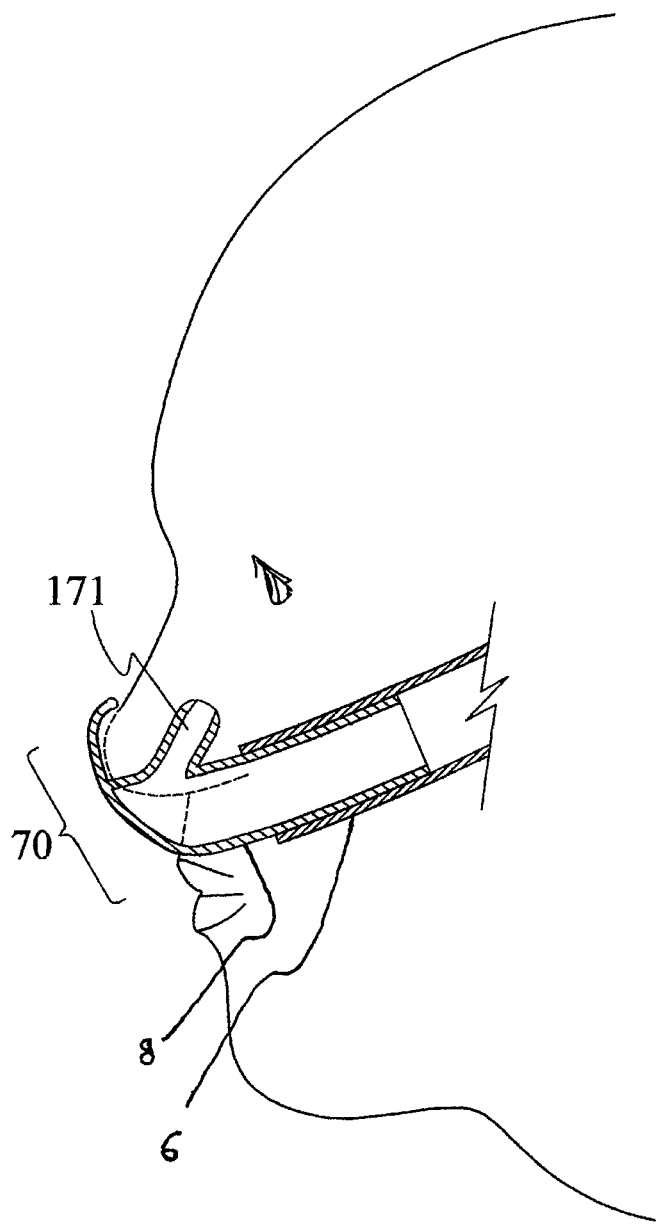
FIG. 12 is a partial section view of a person wearing a nose breathing version of the device in accordance with various embodiments.

FIGS. 11 and 12 show an alternate embodiment of the personal air filter device where instead of the mouthpiece 12 and mouthpiece retaining member 10, a nose piece 170 is substituted in its place. The section view in FIG. 12 shows a nostril interface 171 of the nose piece 170 being inserted into the user's nasal passage. In this way, the user has the choice of either breathing through his or her nose or through his or her mouth when using the device.

FIG. 13 shows the folded out ear support member 16 that holds the air filter holding member 2 onto a person's ear.

FIG. 14 shows a perspective view of an alternate way to hold the air filter holding member 2 onto a person. A spring biased clip 180 is attached to the underside of the air filter holding member 2 in place of the ear pad member and may be clipped onto a person's clothing.

FIG. 15 shows an exploded view of an alternate way of wearing the personal air filter device by attaching the headband 60 between the ear pad holding plate 42 and the back of the air filter holding member 2.

Figure 16:
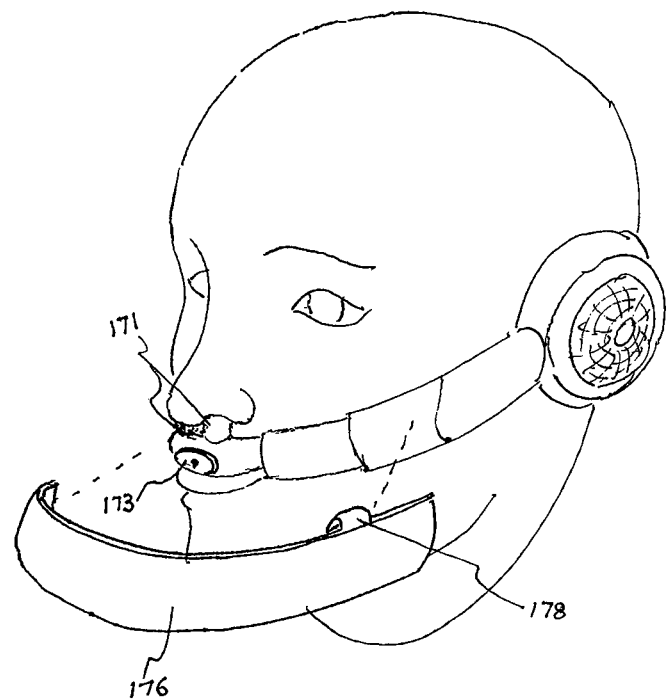
FIG. 16 is an exploded view of a nose piece version of the device in accordance with various embodiments.
Figure 17:
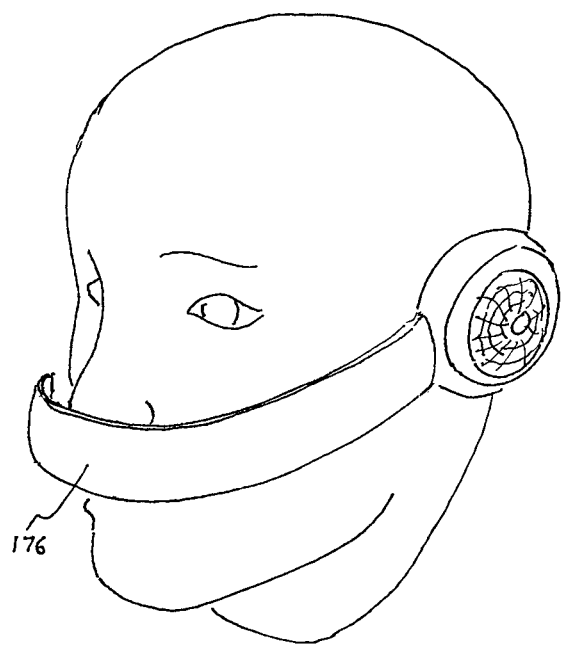
FIG. 17 is a perspective view of a nose piece embodiment of the device with the nose/mouth shield in place.

FIG. 16 shows a person wearing the nose breathing embodiment of the personal air filter device where flexible tubular members 171 are inserted into the user's nostrils. An outflow check valve flap 173 is directed downwards to allow easy escape of air when a nose piece shield 176 is snapped into place using attachment 178 as shown in FIG. 17. Air intake check valve, not shown, is similar to the intake check valve 41 shown in the mouth breathing version of the invention shown in FIG. 6.

Figure 18:
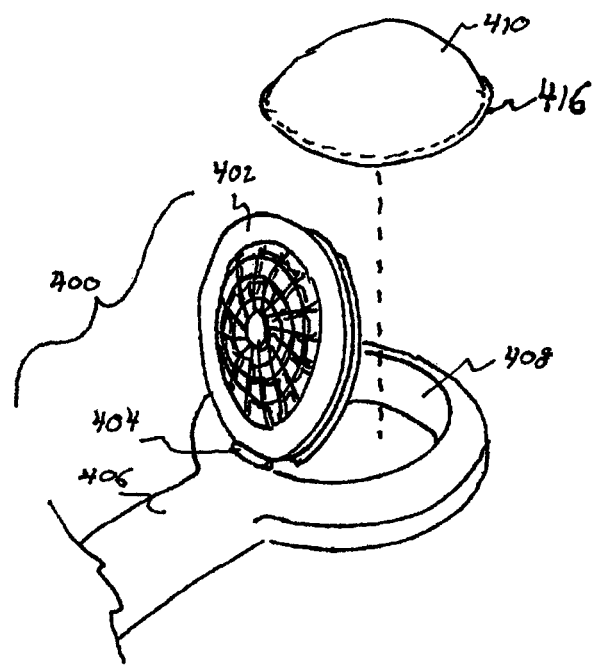
FIG. 18 is an exploded perspective alternate embodiment of the device with a hinged lid and a separate air filter pack.

FIG. 18 shows a partial perspective view of an alternate embodiment of the air filter holding member 400 where the top cover 402 of the air filter holding member 400 is hinged 404 and can be lifted to insert or remove an air filter pack 410 which may be an assembly consisting of a particulate filter material on the outside and a carbon activated material on the inside. The perimeter edge 416 of air filter pack 410 is trapped between the downwardly facing radial rib 414 and the ledge 412 inside filter housing well 408 thereby creating an air tight seal and forcing air entering the personal air filter device to pass through the air filter pack 410.

Figure 19:
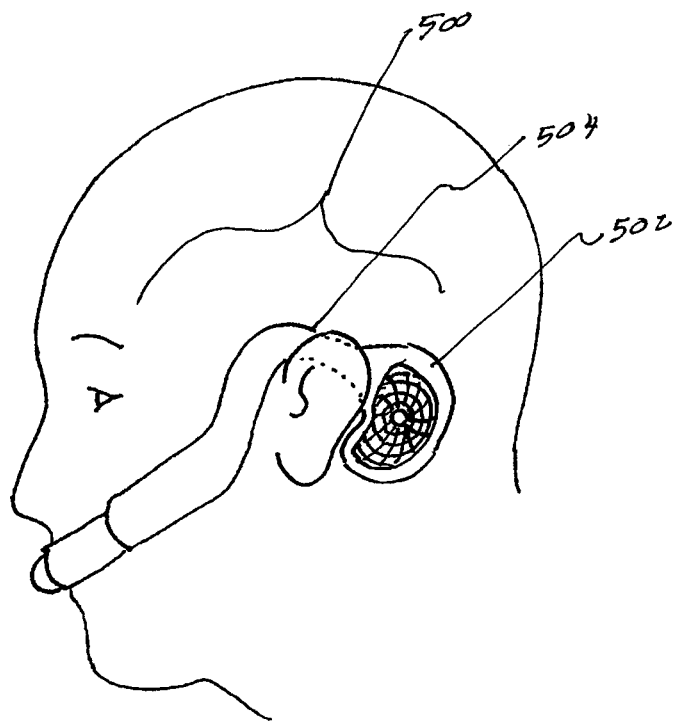
FIG. 19 is a side view of an alternate embodiment of the device with an air filter holding member and an air filter assembly located behind the ear.

FIG. 19 shows an alternate embodiment of the personal air filter device 500 where the air filter holding member 502 is just behind the user's ear and the air tube 504 rests on the top portion of the user's ear where the ear meets the head. This configuration helps balance the weight of the entire assembly so that the weight of the air tube going to the user's mouth and the weight of the air filter holding member are approximately equal.

Figure 20:
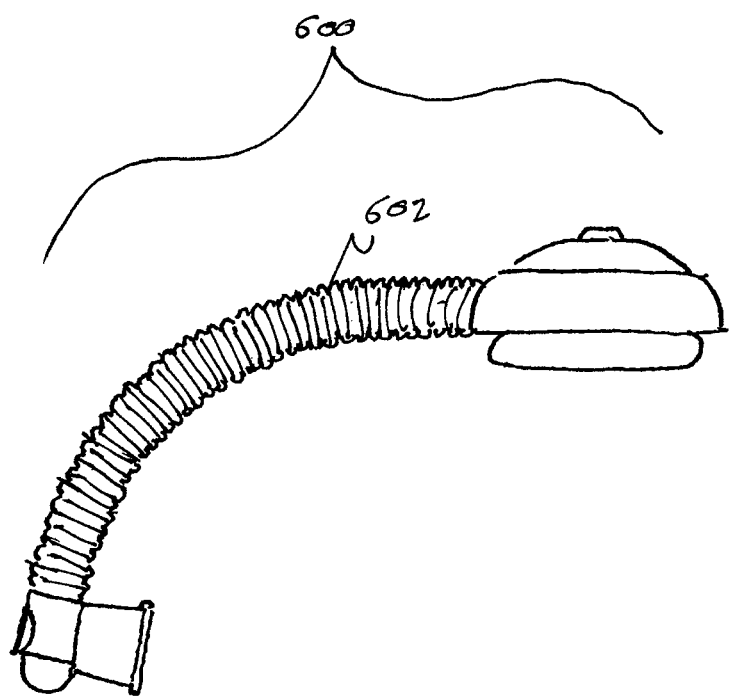
FIG. 20 is a side view of an alternate embodiment of the device with a single flexible air tube.

FIG. 20 shows another alternate embodiment of the personal air filter device 600 where a single flexible air tube 602 is used in place of the telescoping tube configuration shown in the previously described embodiments. This configuration 600 produces cost savings in comparison to the previous embodiment.

Figure 21:
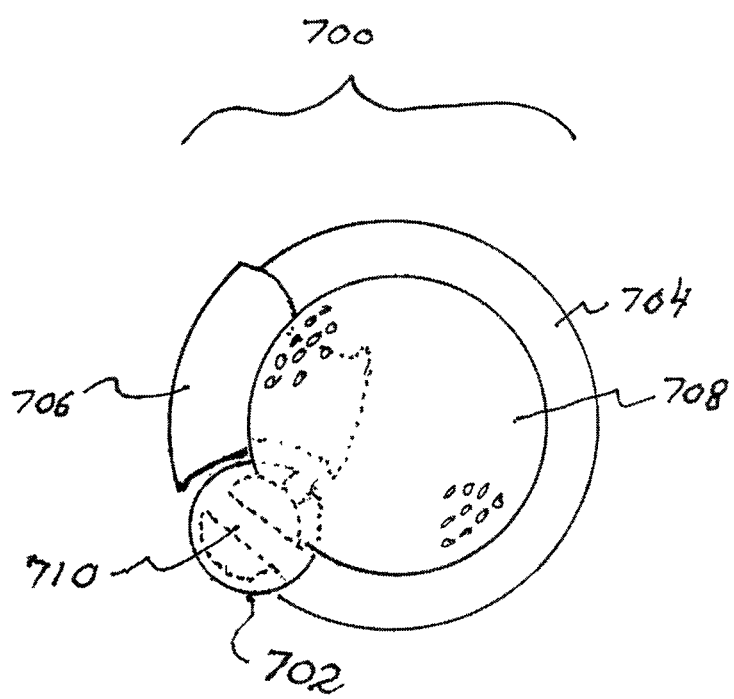
FIG. 21 is a plan view of a ball joint version of the invention in the folded, storage position.
Figure 22:
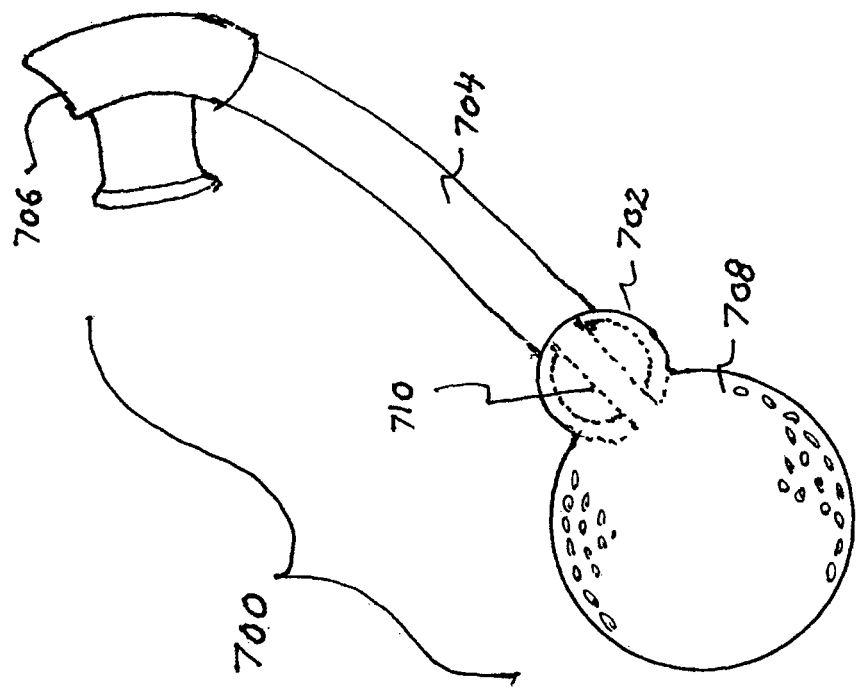
FIG. 22 is a plan view of the ball joint version of the invention in the use position.

FIG. 21 shows a plan view of another embodiment of the device 700 where a flexible tube 704 can wrap around the main air filter holding member 708 forming a compact storage configuration. The ball joint air passageway 702 allows the tube to lie in close contact with the main filter area 708 when in the folded storage position and when the tube 704 is extended out as shown in FIG. 22, the tube 704 and mouthpiece 706 are in the correct position for use. Dotted lines 710 shows the air passage way within the ball valve 702.

Figure 23:
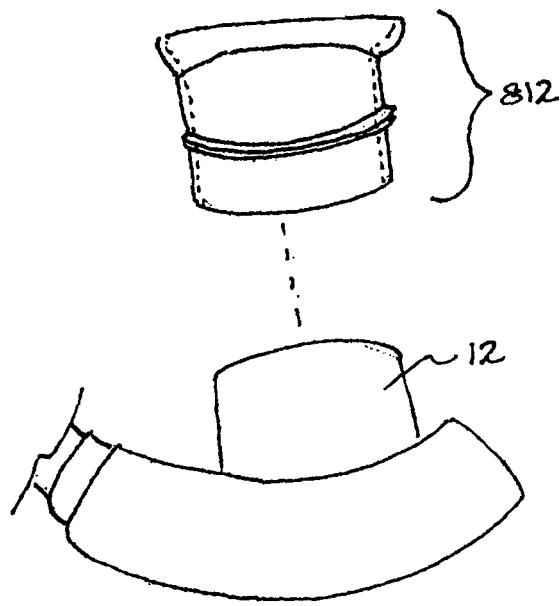
FIG. 23 is an exploded view of the mouth piece with mouthpiece cover.

FIG. 23 shows a plan view of the mouthpiece 12 with the option of a secondary mouthpiece insert cover 812 which is capable of being removably attached to the mouthpiece 12. This allows the user to change mouthpieces as needed, either to install a different size mouthpiece to accommodate differences in mouth size and structure, or to replace a worn or soiled mouthpiece with a new one.

Figure 24:
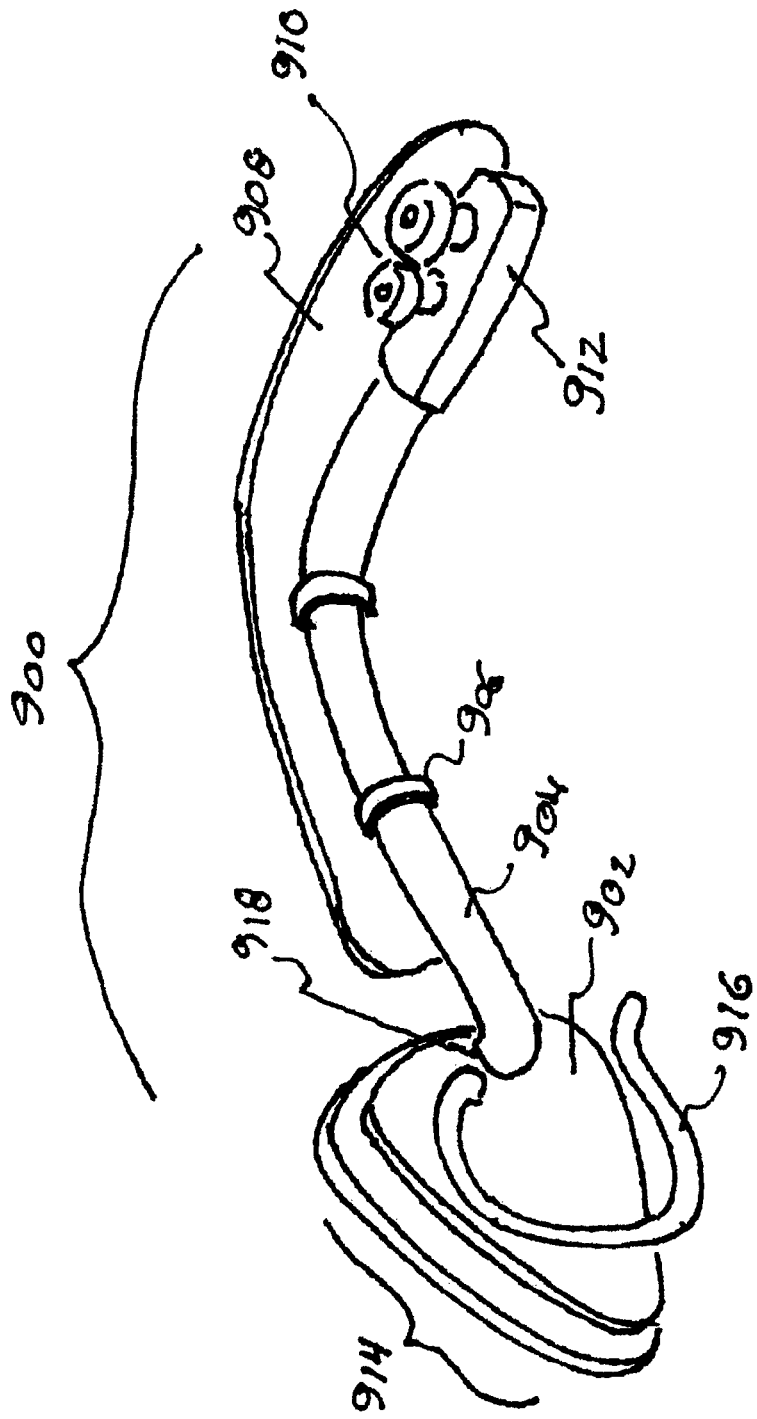
FIG. 24 is a perspective view of an alternate embodiment of the device with nose piece and nose shield in accordance with various embodiments.

FIG. 24 shows a perspective view of another embodiment of the device 900 where the air filter holding member 914 is triangular in shape. The main breathing tube 904 is rotatably attached to the back of the air filter holding member 902 by means of an L shaped joint 918. The curve of the breathing tube 904 is designed to follow the contour of the user's face. The embodiment 900 shown is designed for use with the user's nose. Flexible nostril insert members 910 extend from check valve housing 912 and are inserted into the nose and act to help hold the breathing tube in place during use and prevent ambient air leakage into the nose. A nose concealing panel 908 is held onto breathing tube 904 via retaining clips 906. The concealing panel can also be fixedly attached to the breathing tube or combined with the breathing tube in a single piece. Another version of this embodiment 900 employs a mouthpiece rather than the nosepiece shown in FIG. 24. Ear support member 916 holds the device 900 to the user's head and works as described in earlier versions of the invention.

The above description and drawings show a novel device for a personal air filtration system that can be worn in an unassuming way, without covering major portions of the user's face and yet provide a significant degree of filtering of common outdoor air pollutants.

While the personal air filter device has been described in connection with a number of embodiments, it is not intended to limit the scope of the device to the particular form set forth, but on the contrary, it is intended to cover such alternatives, modifications, and equivalents as may be included within the spirit and scope of the device as defined by the appended claims. For example, although the body of the device is preferably made out of plastic, other materials may similarly be used, such as glass and bio-plastic. In addition, although the shape of the air filter and air filter holder are preferably round, different shapes may be similarly used, such as a triangular, rectangular or heart shaped filter and filter holder. Moreover, the filter case and nose/mouth shield may be decorative in nature, allowing the user to personalize the appearance of the device. It is contemplated that the nose/mouth shield will be produced in many colors, shapes and patterns, again allowing users to personalize the device. Additionally, the filter material can be scented or flavored. The ear piece may include earphones that provide audio to the user of the filter from a Bluetooth enabled device, such as a cellphone, tablet, or laptop computer. In addition, the device may contain a pollutant sensor to indicate when the filter should be replaced. The device may further contain a mechanism to alert the user to the levels of pollution in the area the user is using the device.

What is claimed is:

1. A personal respiratory device comprising:
    an air filter assembly with filter media the air filter assembly configured to provide unpowered filtration of ambient air;
    an air filter holding member;
    an air tube coupled to the air filter holding member;
    a breathing orifice interface connected to an end of the air tube which is opposite the air filter holding member, said breathing orifice interface configured to be inserted into a breathing orifice of an individual for allowing the individual to breathe filtered air flowing through said air tube from said air filter assembly;
    at least one air intake check valve configured for allowing the individual to breathe the filtered air;
    at least one air outflow check valve configured for ensuring that air expelled from lungs of the individual exits the device; and
    a member configured to connect the device to the individual;

wherein the device is configured to extend in only one direction from the breathing orifice so that a face of the individual is not overly obscured by the device when worn.

2. The device as claimed in claim 1 wherein the air filter assembly comprises an air filter cartridge assembly; said air filter cartridge assembly having stacked components including a rigid top cover member, a particulate disk filter member, an activated carbon filter disk member, a rigid lower filter retaining member and a central retaining fastener; said stacked components held together by said central retaining fastener; said air filter cartridge assembly removably retained in said air filter holding member.

3. The device as claimed in claim 2 further comprising a magnet attached to an underside of said central retaining fastener and a ferrous metal plate attached to a center of said central retaining fastener, thereby allowing said air filter cartridge assembly to be held in place by contact of said magnet and said metal plate.

4. The device as claimed in claim 1 wherein the air further comprising, as the breathing orifice interface, a mouthpiece retaining member and a mouthpiece; said mouthpiece retaining member rotatably or fixedly attached to said air tube; said mouthpiece rotatably or fixedly attached to said mouthpiece retaining member; said mouthpiece configured to be inserted into a mouth of the individual; said at least one air intake check valve situated near the end of said air tube nearest the mouthpiece; said at least one air outflow check valve situated in said mouthpiece retaining member.

5. The device as claimed in claim 4 wherein the mouthpiece has a removable and replaceable mouthpiece cover.

6. The device as claimed in claim 1 further comprising, as the breathing orifice interface, a nose piece; said nose piece rotatably or fixedly attached to said air tube; tubular inserts of said nose piece configured to be inserted into nostrils of the individual; said at least one air intake check valve situated near the end of said air tube nearest the nose piece; said at least one air outflow check valve situated in said nose piece.

7. The device as claimed in claim 6 wherein the tubular inserts have removable and replaceable covers.

8. The device as claimed in claim 1 wherein the member comprises an ear support member; said ear support member being an inverted J shape and attached on at least one end to said air filter holding member; said ear support member capable of being hung over an ear of said individual to support said air filter holding member.

9. The device as claimed in claim 1 further comprising a headband; said headband attached to said air filter holding member and configured to allow said air filter holding member to be removably attached to a head of the individual.

10. The device as claimed in claim 9 further including an ear pad attached to a side of the said air filter holding member adapted to be closest to the head of the individual, the ear pad configured to be in contact with an ear of the individual.

11. The device as claimed in claim 10 further comprising a speaker member incorporated into the ear pad.

12. The device as claimed in claim 10 wherein the side of the air filter holding member adapted to be closest to the head of the individual has an indentation configured to fit an earphone device underneath it.

13. The device as claimed in claim 1 further comprising a clip; said clip being attached to said air filter holding member and configured to allow said device to be removably attached to clothing of the individual, a neck strap, a chain, a headband or other accessory.

14. The device as claimed in claim 1 wherein the air tube comprises a first air tube member, a second air tube member, and a third air tube member; said first air tube member fixed to said air filter holding member thereby allowing air to flow from said air filter assembly to said first air tube member; said second air tube member rotatably attached to said first air tube member; and said third air tube member slidably attached in a telescoping fashion to said second air tube member.

15. The device as claimed in claim 1 further comprising a shield member that attaches to the air tube and curves bendably over the breathing orifice interface.

16. The device as claimed in claim 1 wherein a shield member is combined with the air tube as one piece.

17. The device as claimed in claim 1 wherein said air filter holding member is configured for wearing behind at least one ear of the individual.

18. The device as claimed in claim 1 wherein the air filter holding member further comprises an air permeable lid that opens and closes to allow the air filter media to be inserted or removed from the air filter holding member.

19. The device as claimed in claim 1 wherein the air tube comprises a first air tube member and a second air tube member; said first air tube member fixed to said air filter holding member thereby allowing air to flow from said air filter assembly to said first air tube member; said second air tube member slidably attached in a telescoping fashion to said first air tube member so that the second air tube member can be slid in or out of said first air tube member allowing a length of the combined air tube to be adjusted to accommodate a specific head size and ear location of said individual.

20. The device as claimed in claim 1 further comprising a fragrance element.

21. The device as claimed in claim 1 further comprising a pollution sensor device to determine when the air filter assembly should be replaced.

22. The device as claimed in claim 1 further comprising a pollution sensor mechanism that informs the individual of pollution levels.

23. The device as claimed in claim 1 further comprising a ball valve built into said air tube and rotatably attached to said air filter holding member thereby allowing said air tube to reside in close proximity to said air filter holding member when not in use, and to rotate out when in use.

24. The device as claimed in claim 1 wherein the air tube is curved at a sufficient angle to follow curvature of a human head from an ear to a nose and/or a mouth.

* * * * *